United States Patent

Bosslet et al.

[11] Patent Number: 6,020,315
[45] Date of Patent: Feb. 1, 2000

[54] PREPARATION HAVING INCREASED IN VIVO TOLERABILITY

[75] Inventors: Klaus Bosslet, Gaithersburg, Md.; Jörg Czech, Marburg, Germany; Manfred Gerken, Marburg, Germany; Rainer Straub, Marburg, Germany; Matthias Blumrich, Wettenberg, Germany

[73] Assignee: Hoechst Aktiengesellschaft, Frankfurt am Main, Germany

[21] Appl. No.: 09/076,878

[22] Filed: May 13, 1998

[30] Foreign Application Priority Data

May 15, 1997 [DE] Germany ............................ 197 20 312

[51] Int. Cl.$^7$ .............................. A61K 31/70; C07H 5/06; C07H 15/244
[52] U.S. Cl. ............................... 514/34; 514/25; 514/42; 536/4.1; 536/6.4; 536/29.1
[58] Field of Search .................... 514/25, 34, 42; 536/4.1, 6.4, 29.1

[56] References Cited

U.S. PATENT DOCUMENTS

| | | | |
|---|---|---|---|
| 5,561,119 | 10/1996 | Jacquesy et al. | 514/34 |
| 5,621,002 | 4/1997 | Bosslet et al. | 514/451 |
| 5,710,134 | 1/1998 | Bosslet et al. | 514/34 |

FOREIGN PATENT DOCUMENTS

| | | |
|---|---|---|
| 0 540 859 A1 | 8/1988 | European Pat. Off. . |
| 0 511 917 A1 | 4/1992 | European Pat. Off. . |
| 0 642 799 A1 | 8/1994 | European Pat. Off. . |
| 0 595 133 A2 | 10/1995 | European Pat. Off. . |
| 0 751 144 A1 | 1/1997 | European Pat. Off. . |
| 0 795 334 A2 | 2/1997 | European Pat. Off. . |

OTHER PUBLICATIONS

Bosslet et al. "Fusion Protein–Mediated Tumor Selective Prodrug Activation" from *Contributions to Oncology*, (Eds. Huber & Queisser), vol. 48: 160–169, 1995.
Bosslet et al. *Tumor Targeting*, vol. 1: 45–50, 1995.
Bosslet et al. *Cell Biophys.*, vol. 24/25: 51–63, 1994.
Haisma et al. *Cell Biophys.*, vol. 24/25: 185–192, 1994.
Bosslet, Klaus, et al., "Tumor–selective Prodrug Activation by Fusion Protein–mediated Catalysis," *Cancer Research*, 54 (1994), pp. 2151–2159.
Gesson, J.P., et al., "Prodrugs of anthracyclines for chemotherapy via enzyme–monoclonal antibody conjugates," *Anti–Cancer Drug Design*, 9 (1994), pp. 409–423.
Houba, Pieter H.J., et al., "Characterization of Novel Anthracyline Prodrugs Activated by Human β–glucuronidase for Use in Antibody–Directed Enzyme Prodrug Therapy," *Biochemical Pharmacology*, 52 (1996), pp. 455–463.
Leenders, Ruben G.G., et al., "β–Glucuronyl Carbamate Based Pro–moieties Designed for Prodrugs in ADEPT," *Tetrahedron Letters*, 36 (1995), pp. 1701–1704.
Sinhababu, Anchintya K., et al., "Review Prodrugs of anticancer agents," *Advanced Drug Delivery Reviews*, 19 (1996), pp. 241–273.
Fiebig et al., Comparison of Tumor Response in Nude Mice and in the Patients, *Behring Inst. Mitt.*, No. 74, pp. 343–352 (1984).

*Primary Examiner*—Howard C. Lee
*Attorney, Agent, or Firm*—Finnegan, Henderson, Farabow, Garrett & Dunner, L.L.P.

[57] ABSTRACT

A preparation having increased in vivo tolerability comprising a glycosyl-Y[—C(=Y)—X—]$_p$—W(R)$_n$—X—C(=Y)-active compound, sugar or sugar alcohol and, optionally divalent ions, and a pharmaceutically tolerable carrier.

14 Claims, No Drawings

PREPARATION HAVING INCREASED IN VIVO TOLERABILITY

The invention aims to improve the tolerability of a pharmaceutically active compound in a patient and optionally to increase the therapeutic efficacy. This is effected by chemically modifying the active compound. The therapy of malignant tumors, inflammatory disorders and autoimmune disorders is associated, in addition to the inadequate activity of the therapeutics, with severe side effects. These unwanted side effects are largely due to the excessively low in vivo tolerability of the active compounds employed.

The invention therefore relates to a composition comprising:
(1) a compound of the formula I, or a physiologically tolerable salt thereof:

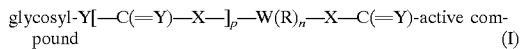

glycosyl-Y[—C(=Y)—X—]$_p$—W(R)$_n$—X—C(=Y)-active compound (I)

in which
glycosyl is an enzymatically cleavable poly-, oligo- or monosaccharide,
W is an aromatic or a heteroaromatic or an aliphatic having conjugated double bonds or an amino acid derivative which cyclizes after cleavage of the glycosyl radical, where the substituent,
R is a hydrogen atom, methyl, methoxy, carboxyl, CN, methylcarbonyl, hydroxyl, nitro, fluorine, chlorine, bromine, sulfonyl, sulfonamide or sulfon-($C_1$–$C_4$)-alkylamide,
p is 0 or 1,
n is an integer,
X is an oxygen atom, NH, methyleneoxy, methyleneamino or methylene-($C_1$–$C_4$)-alkylamino and
Y is an oxygen atom or NH, and the active compound is a compound having biological action linked via a hydroxyl, amino or imino group,
(2) sugar or sugar alcohol; and
(3) a pharmaceutically tolerable carrier.

The term "active compound," as used in the specification and the attached claims, is understood to mean compounds such as an anthracycline (preferably doxorubicin), 4'-epidoxorubicin, 4- or 4'-deoxydoxorubicin, etoposide, epothilone A-C, N-bis(2-chloroethyl)-4-hydroxyaniline, 4-hydroxycyclophosphamide, vindesine, vinblastine, vincristine, terfenadine, terbutaline, fenoterol, salbutamol, muscarine, oxyphenbutazone, salicylic acid, p-aminosalicylic acid, 5-fluorouracil, methotrexate, diclofenac, flufenamic acid, 4-methylaminophenazone, theophylline, nifedipine, mitomycin C, mitoxantrone, camptothecin and camptothecin derivatives, N-[4-(9-acridinylamino)-3-methoxy-phenyl]-methansulfonamide ("m-AMSA"), taxol or other taxanes, nocodaxol, colchicine, fexofenadine, cyclophosphamide, rachelmycin, cisplatin, melphalan, bleomycin, nitrogen mustard gas, phosphoramide mustard gas, verrucarin A, neocarcinostatin, calicheamicin, dynemicin, esperamicin A, quercetin, genistein, erbstatin, tyrphostin, rohitukin derivative, retinoleic acid, butyric acid, phorbol ester, dimethyl sulfoxide, aclacinomycin, progesterone, buserelin, tamoxifen, mifepristone, onapristone, N-(4-aminobutyl)-5-chloro-2-naphthalenesulfonamide, pyridinyloxazol-2-one, quinolyl- or isoquinolyloxazol-2-one, staurosporin, ethanolamine, verapamil, forskolin, 1,9-dideoxyforskolin, quinine, quinidine, reserpine, 18-O-(3,5-dimethoxy-4-hydroxybenzoyl)-reserpate, lonidamine, buthionine sulfoximine, diethyl dithiocarbamate, cyclosporin A, rapamycin, azathioprine, chlorambucil, hydroxycrotonamide derivative 2, leflunomide, 15-deoxyspergualine, FK 506, ibuprofen, indomethacin, aspirin, sulfasalazine, penicillamine, chloroquine, dexamethasone, prednisolone, mefonamidic acid, paracetamol, 4-aminophenazone, muskosine, orciprenaline, isoprenaniline, amiloride, p-nitrophenyl guanidine benzoate, or their derivatives in which one or more hydroxyl, amino or imino groups have been additionally substituted.

As used herein, "n" is an integer, preferably from 1 to 8, most preferably from 1 to 4.

The term "sugar" is understood to include aldoses having 3 to 7 carbon atoms, which can belong to the D or L series; this term also includes amino sugars or uronic acids. Examples which may be mentioned are glucose, mannose, fructose, galactose, ribose, erythrose, glyceraldehyde, sedoheptulose, glucosamine, galactosamine, glucuronic acid, galacturonic acid, gluconic acid, galactonic acid or mannonic acid.

The term "sugar alcohols" are compounds formed, for example, by the reduction of the above-mentioned sugars, particularly glucitol, mannitol, sorbitol, glycerol or inositol.

Suitable physiologically tolerable salts of the compounds of the formula I are, for example, alkali metal, alkaline earth metal and ammonium salts including those of organic ammonium bases and salts of the protonated amino acid radicals. Alkali metal salts such as sodium or potassium salts are preferred.

In particular, the preparations according to the invention additionally contain divalent ions. The term "divalent ions" is understood as meaning, for example, divalent metal ions of Ca, Mg, Fe, Cu or Ni.

Compounds of the formula I are preferably employed in which
W is a phenyl radical or a polysubstituted phenyl radical, and where the substituent,
R is a hydrogen atom, methyl, methoxy, carboxyl, methyloxycarbonyl, CN, hydroxyl, nitro, fluorine, chlorine, bromine, sulfonyl, sulfonamide or sulfon-($C_1$–$C_4$)-alkylamide,
p is zero or 1,
n is 1 to 4,
X is an oxygen atom, NH, methyleneoxy, methyleneamino or methylene-($C_1$–$C_4$)-alkylamino,
Y is an oxygen atom or NH, and the active compound is a compound as described above.

Compounds of the formula I are particularly preferably employed in which glycosyl is a poly-, oligo- or monosaccharide, in particular an alpha- or beta-O-glycosidically linked D-glucuronyl, D-glucopyranosyl, D-galactopyranosyl, N-acetyl-D-glucosaminyl, N-acetyl-D-galactosaminyl, D-mannopyranosyl or L-fucopyranosyl radical,
W is a phenyl radical or a monosubstituted phenyl radical, where the substituent,
R is methoxy, methyloxycarbonyl, CN, hydroxyl, nitro, fluorine, chlorine, bromine, sulfonyl or sulfonamide and the others are a hydrogen atom,
X is O, NH, methyleneoxy, methyleneamino or methylenemethylamino,
Y is O or NH, and the active compound is a compound as described above.

Compounds are preferably employed wherein the glycosyl radical can be cleaved by enzymatic hydrolysis, the spacer (—Y[—C(=Y)—X—]$_p$—W(R)$_n$—X—C(=Y)-portion of formula I) can be cleaved spontaneously by chemical hydrolysis, and the active compound is a pharmaceutical or one of its derivatives obtained by introduction of additional hydroxyl, amino or imino groups. The compound of this invention is more hydrophilic than the active compound, and effects fewer toxic reactions in vivo than the active compound as such.

This invention is applicable to a wide variety of pharmaceuticals, with the goal of easing the toxic side effects of these drugs upon introduction into the body. Possible active compounds include antitumor agents, standard cytostatics, antimetabolites, substances that intercalate DNA, inhibitors of topoisomerase I +II, tubulin inhibitors, alkylating agents, compounds that inactivate ribosomes, tyrosine phosphokinase inhibitors, differentiation inducers, hormones, hormone agonists or hormone antagonists, substances which modify the pleiotropic resistance to cytostatics, calmodulin inhibitors, protein kinase C inhibitors, P-glycoprotein inhibitors, modulators of mitochondrially bound hexokinase, inhibitors of γ-glutamylcysteine synthetase or of glutathione S-transferase, inhibitors of superoxide dismutase, inhibitors of the proliferation-associated protein (defined by the Mab Ki67) in the cell nucleus of cells which are dividing, the active compound is a substance which exerts immunosuppressant effects, standard immunosuppressants, macrolides, nonsteroidal antiinflammatory substances, slow-acting antirheumatic drugs, steroids, antiinflammatory, analgesic or antipyretic substances, derivatives of an organic acid, nonacidic analgesics or antiinflammatories, local anesthetics, antiarrhythmics, $Ca^{++}$ antagonists, antihistaminics, phosphodiesterase inhibitors, parasympathomimetics, sympathomimetics or substances having inhibitory action on human urokinases.

Specific examples of these active compounds include, but are not limited to, 5-fluorocytidine, 5-fluorouridine, cytosine arabinoside or methotrexate, doxorubicin, daunomycin, idarubicin, epirubicin or mitoxantrone, camptothecin and camptothecin derivatives, etoposide or M-AMSA, vincristine, vinblastine, vindesine, taxol and taxanes, nocodaxole, colchicine or etoposide, cyclophosphamide, mitomycin C, rachelmycin, cisplatin, phosphoramide mustard gas, melphalan, bleomycin, nitrogen mustard gas or N-bis(2-chloroethyl-4-hydroxyaniline), neocarcinostatin, calicheamicin, epothilone A-C, dynemicin or esperamicin A, verrucarin A, quercetin, genistein, erbstatin, tyrphostine or rohitukin derivative, retinoleic acid, butyric acid, phorbol ester, DMSO or aclacinomycin, progesterone, buserelin, tamoxifen or onapristone, cyclosporin A, rapamycin, FK 506, azathiprine, methotrexate, cyclophosphamide or chlorambucil, or oxyphenbutazone.

Additional preferred compounds include compounds wherein the glycosyl radical is an alpha- or beta-O-gyclosidically linked D-glucuronyl, D-glucopyranosyl, D-galactopyranosyl, N-acetyl-D-glucosaminyl, N-acetyl-D-galactosaminyl, D-mannopyranosyl or L-fucopyranosyl radical.

Specific embodiments of component 1 of this invention include N-[4-O-(beta-D-glucopyranosyluronic acid)-3-nitrobenzyloxycarbonyl]-doxorubicin sodium salt (Compound II), 4'-O-[4-(alpha-D-glucopyranosyloxy) phenylaminocarbonyl]etoposide, N-[4-O-(beta-D-glucopyranosyluronic acid)-3-chlorobenzyloxycarbonyl] doxorubicin sodium salt, N-[4-O-(beta-D-glucopyranosyluronic acid)-3-fluorobenzyloxycarbonyl]-doxorubicin sodium salt, N-[4-O-(beta-D-glucopyranosyluronic acid)-3-nitrobenzyloxycarbonyl]-daunorubicin sodium salt, N-[4-O-(beta-D-glucopyranosyluronic acid)-3-chlorobenzyloxycarbonyl]-daunorubicin sodium salt, N-[4-O-(alpha-D-galactopyranosyl)-3-nitrobenzyloxycarbonyl]daunorubicin, N-[4-O-(alpha-D-galactopyranosyl)-3-chlorobenzyloxycarbonyl]daunorubicin, N-[4-O-(alpha-D-galactopyranosyl)-3-fluorobenzyloxycarbonyl]daunorubicin, N-[4-O-(beta-D-glucopyranosyluronic acid)-3-nitro-benzyloxycarbonyl]-doxorubicin sodium salt, N-[2-O-(beta-D-glucopyranosyluronic acid)-5-chlorobenzyloxycarbonyl]-doxorubicin sodium salt, N-[2-O-(beta-D-glucopyranosyluronic acid)-5-fluorobenzyloxycarbonyl]-doxorubicin sodium salt, N-[2-O-(beta-D-glucopyranosyluronic acid)-5-nitrobenzyloxycarbonyl]-daunorubicin sodium salt, N-[2-O-(beta-D-glucopyranosyluronic acid)-5-chlorobenzyloxycarbonyl]-daunorubicin sodium salt, N-[2-O-(alpha-D-galactopyranosyl)-5-nitrobenzyloxycarbonyl]-daunorubicin, N-[2-O-(alpha-D-galactopyranosyl)-5-chlorobenzyloxycarbonyl]daunorubicin, N-[2-O-(alpha-D-galactopyranosyl)-5-fluorobenzyloxycarbonyl]-daunorubicin, 4'-O-[4-(beta-D-glucopyranosyloxy) phenylaminocarbonyl]etoposide, 4'-O-[4-(alpha-D-galactapyranosyloxy)phenylaminocarbonyl]etoposide, 4'-O-[4-(beta-D-glucuronyloxy)phenylaminocarbonyl] etoposide, 4'-O-[4-(beta-D-glucuronyloxy)-3-nitrobenzylaminocarbonyl]etoposide, 4'-O-[4-(beta-D-glucuronyloxy)-3-chlorobenzylaminocarbonyl]etoposide, 1-N-[4-(beta-D-glucuronyloxy)benzyloxycarbonyl] mitomycine C, 14-O-[4-(beta-D-glucuronyloxy)-3-nitrobenzylaminocarbonyl]doxorubicine, 4-O-[4-(beta-D-glucuronyloxy)benzylaminocarbonyl]-4-hydroxy-1-N-(bis-2-chloroethyl)aniline, 4-O-[4-beta-D-glucuronyloxy) benzylaminocarbonyl]terfenadine, 3'-O-[4-(beta-D-glucuronyloxy)benzylaminocarbonyl]terbutaline, 3'-O-[4-(beta-D-glucuronyloxy)benzylaminocarbonyl]fenoterole, 1"-O-[4-(beta-D-glucuronyloxy)benzylaminocarbonyl] salbutamol, 3-O-[4-(beta-D-glucuronyloxy) benzylaminocarbonyl]muscarine, 4'-O-[4-(beta-D-glucuronyloxy)benzylaminocarbonyl)oxphenbutazone, 2-O-[4-(beta-D-glucuronyloxy)benzylaminocarbonyl) salicylic acid, N-[4-(beta-D-glucuronyloxy) benzyloxycarbonyl)diclofenac, N-[4-(beta-D-glucuronyloxy)benzyloxycarbonyl]flufenamic acid, 4-N-[4-(beta-D-glucuronyloxy)benzyloxycarbonyl]-4-methylaminophenazone, 7-N-[4-beta-D-glucuronyloxy) benzyloxycarbonyl]theophylline, 1-N-[4-(beta-D-glucuronyloxy)benzyloxycarbonyl]nifedipine, [4-(β-D-glucuronyloxy)-3-nitrobenzyl]-2-[1-cyano-1-(N-4-trifluoro-methylphenyl)carbamoyl]propene-1-ylcarbonate, 3'-N-[4-N-(alpha-D-galactosyloxycarbonyl)-4-aminobenzy-oxycarbonyl]-doxorubicin, 9-O-[4-(beta-D-glucuronyloxy)-3-chlorobenzyloxycarbonyl]quinine or 18-O-[3,5-dimethoxy-4-[4-beta-D-glucuronyloxy)-3-chlorobenzyl-oxycarbonyl]benzoyl]reserpate respectively.

The compound II is N-[4-O-(beta-D-glucopyranosyluronic acid)-3-nitrobenzyloxycarbonyl]-doxorubicin sodium salt, and its structure is:

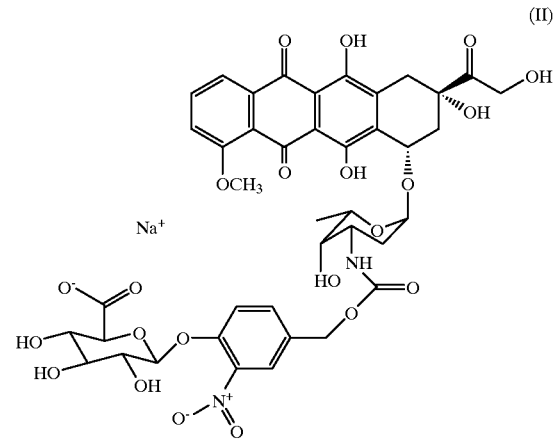

(II)

Compound II is particularly preferably employed as an active compound in a solution also comprising mannitol as a sugar alcohol and $Ca^{2+}$ as a divalent ion. The compound II is employed in an amount from 1 to 1000 mg/kg of live weight, preferably from 5 to 500 mg/kg. If a solution composition is used, mannitol is employed in an amount from 1 mg/mL to 150 mg/mL, preferably from 10 to 100 mg/mL, most preferably 50 mg/mL. In a solution preparation, $Ca^{2+}$ ions, for example as $CaCl_2$, are employed in an amount from 0.01 mg/mL to 10 mg/mL, preferably from 0.05 to 2 mg/mL, most preferably 0.4 mg/mL of $CaCl_2 \times 2H_2O$.

The compound of the formula I is prepared, for example, as described in EP 0 751 144.

The preparation according to the invention is suitable, for example, for the treatment of acute immunological events such as sepsis, allergy, graft-versus-host and host-versus-graft reactions autoimmune disorders, in particular rheumatoid arthritis, systemic lupus erythematosus, multiple sclerosis psoriasis, atopic dermatitis, asthma, urticaria, rhinitis, uveitis liver fibrosis, cystic fibrosis, colitis cancers such as lung cancer, leukemia, ovarian cancer, sarcomas, Kaposi's sarcoma, meningioma, intestinal cancer, cancer of the lymph nodes, brain tumors, breast cancer, cancer of the pancreas, cancer of the prostate or skin cancer.

The solid preparation according to the invention can include compositions where the components (1), (2), and optionally divalent ions, are thoroughly mixed. Or, compositions are contemplated in which the components are separate from one another and can therefore be administered sequentially to the human or animal patient. This is useful if the administration is difficult due to the spatial dimensions of the required dose. This applies particularly to the oral forms, since frequently in the case of older patients there is an aversion to large tablets or capsules. If components (1), (2), and optionally divalent ions, are administered separately, it is imperative that these separate pharmaceutical forms are taken at the same time. In this case, it is possible for different forms, for example tablets and capsules, to be used for the different components.

The invention further relates to a process for the production of the composition according to the invention, which comprises processing the components (1), (2), optionally divalent ions, and a pharmaceutical carrier to give a pharmaceutical administration form.

The preparation according to the invention can be present as a dose unit in the form of pharmaceutical forms such as capsules (including microcapsules), tablets (including coated tablets and pills) or suppositories, where when using capsules the capsule material can assume the function of the carrier and the contents can be present, for example, as a powder, gel, emulsion, dispersion or solution. It is particularly advantageous and simple, however, to prepare oral (peroral) formulations containing the three components (1), (2) and, optionally, divalent ions, which contain the calculated amounts of the active compounds together with each desired pharmaceutical carrier. An appropriate formulation can also be used for the transmucosal therapy including the use of suppositories for rectal therapy. Transdermal administration in the form of ointments, pastes, and creams or oral administration of solutions which contain the preparation according to the invention is also possible. The compounds of formula I can also be present as a lyophilizate which is reconstituted before administration using a solution, for example, comprising 5% mannitol and 0.4 mg/mL of $CaCl_2 \times 2H_2O$, (pH approximately 7).

In addition to the active compounds, ointments, pastes, creams and powders can contain a customary excipient, e.g., animal and vegetable fats, waxes, paraffins, starch, tragacanth, cellulose derivatives, polyethylene glycols, silicones, bentonites, talc, zinc oxide, lactose, silicic acid, aluminum hydroxide, calcium silicate and polyamide powder, or mixtures of these substances.

The tablets, pills or granule bodies can be prepared by customary processes such as pressing, dipping or fluidized bed processes or pan coating and contain vehicles and other customary auxiliaries such as gelatin, agarose, starch, (e.g., potato, corn or wheat starch), cellulose such as ethyl cellulose, silica, various sugars such as lactose, magnesium carbonate and/or calcium phosphates. The coating solution usually consists of sugar and/or starch syrup and usually additionally contains gelatin, gum arabic, polyvinylpyrrolidone, synthetic cellulose esters, surface-active substances, plasticizers, pigments and similar additives according to the prior art. For the production of the preparations, any customary flow regulator, glidant or lubricant such as magnesium stearate and release agents can be used.

The dose to be used is, of course, dependent on various factors such as the living being to be treated (human or animal), age, weight, general state of health, severity of symptoms, disorder to be treated, possible concomitant disorders (if present), nature of the concomitant treatment with other pharmaceuticals, and frequency of treatment. The dosages are administered, for example, once to three times per week (e.g., intravenously).

The amount of the active components per dose naturally depends on the number of individual doses to be taken and also on the illness to be treated. The individual dose can also consist of several dose units administered simultaneously.

EXAMPLES

Pharmacological Testing.

The experimental animals used were tumor-bearing nude mice of the NMRI breeding strain having a bodyweight of 17 to 25 g. Six to eight animals were employed per experimental group. The animals received an i.v. administration of the compound II in dissolved form with physiological saline solution (dose of compound II as described in Table 1 in 0.9% NaCl), mannitol (dose of compound II as described in Table 1 in a 5% strength mannitol solution in water pH 7), and a preparation according to the invention comprising compound II, $CaCl_2$ and mannitol (dose of compound II as described in Table 1 in a 5% strength mannitol solution with 0.4 mg of $CaCl_2 \times 2H_2O$.

Administration was carried out on the 1st, 4th and 8th day. The weight of the animals and the growth of the Lovo tumor is determined at 3 to 4 day intervals during the entire experiment. The survival rate was recorded daily. Table 1 shows the results.

TABLE 1

| Pharmaceutical formulation | Dose mg/kg (3x) | Delay in growth of the tumor T-C | | Minimum T/C Ratio | | Mean value of the minimum weight | | Dead animals | |
|---|---|---|---|---|---|---|---|---|---|
| | | (200%) | (400%) | (%) | (Day) | (%) | (Day) | (%) | (Day) |
| Physiological | 225 | 3.9 | 19.3 | 40 | 41 | 76 | 9 | 33 | 6.11 |

TABLE 1-continued

| Pharmaceutical formulation | Dose mg/kg (3x) | Delay in growth of the tumor T-C | | Minimum T/C Ratio | | Mean value of the minimum weight | | Dead animals | |
|---|---|---|---|---|---|---|---|---|---|
| | | (200%) | (400%) | (%) | (Day) | (%) | (Day) | (%) | (Day) |
| saline solution | 350 | n.a. | n.a. | 85 | 4 | 78 | 4 | 100 | 4.8 |
| Mannitol | 350 | 17.3 | 18.8 | 17 | 14 | 72 | 8 | 17 | 19 |
| Ca/Mannitol | 400 | 19.6 | 28 | 13 | 23 | 82 | 10 | 0 | |

"n.a." means not achieved.

T-C (200%) means: doubling time (in days) of the tumor (tumor volume) under treatment with compound II in the corresponding preparation minus doubling time (in days) of the tumor under treatment with the corresponding preparation without compound II.

T-C (400%) means: quadrupling time (in days) of the tumor (tumor volume) under treatment with compound II in the corresponding preparation minus quadrupling time (in days) of the tumor under treatment with the corresponding preparation without compound II.

Minimum T/C ratio (%) means: lowest % value of tumor growth of the therapy group in comparison to the control group.

Minimum T/C ratio (day) means: day on which the tumor growth of the therapy group is lowest in comparison to the control group.

Mean value of the minimum weight (%) means: lowest average body weight observed with respect to body weight before therapy.

Mean value of the minimum weight (Day) means: day after start of experiment where body weight was lowest with respect to body weight before therapy.

Dead animals (%) means: percent of experimental group deceased.

Dead animals (Day) means: average life expectancy (in days) over the course of the experiment.

Only a weak antitumor effect was achieved by i.v. administration of compound II in physiological saline solution at a dose of 3×225 mg/kg. T-C (200%): 3.9 days. The weight decrease (a measure of the side effects of compound II), however, was relatively severe (24% weight decrease and 33% dead animals). The i.v. administration of 3×350 mg/kg of the compound II in physiological saline solution resulted in the rapid death of all experimental animals. Administration of 3×350 mg/kg of the compound II in mannitol resulted in marked antitumor effects (T-C (200%):17.3 days) and a moderate tolerability (weight decrease 28% and 17% dead animals). Administration of 3×400 mg/kg of the compound II in Ca/mannitol induced strong antitumor effects (T-C (200%): 19.6 days) and was highly tolerable for the experimental animals (weight decrease 18%, no dead animals).

Similar advantageous observations were made in experiments in Macaca fascicularis monkeys after i.v. administration of 3×120 mg/kg of compound II in the Ca/mannitol solution. The animals survived this extremely high dose without serious signs of side effects. A maximum of 1×40 mg/kg was tolerated in a solution of the compound II in 0.1M phosphate buffer, pH 7.35. These studies confirm that the compound II is not only significantly more tolerable in the Ca/mannitol solution according to the invention, but is also markedly more active.

Furthermore, it is well-known in the art that chemotherapeutic experiments on these animals have strong predictive power for anti-tumor drug efficacy in humans. See, for example, Fiebig, et al.; Behring Institut Mitteilungen, 74, 343–352 (1984).

We claim:
1. A composition comprising:

(1) a compound of the formula I, or a physiologically tolerable salt thereof:

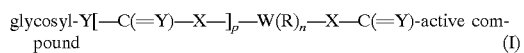

in which glycosyl is an enzymatically cleavable poly-, oligo- or monosaccharide, W is an aromatic or a heteroaromatic or an aliphatic having conjugated double bonds or an amino acid derivative which cyclizes after cleavage of the glycosyl radical, where the substituent, R is a hydrogen atom, methyl, methoxy, carboxyl, CN, methylcarbonyl, hydroxyl, nitro, fluorine, chlorine, bromine, sulfonyl, sulfonamide or sulfon-$(C_1-C_4)$-alkylamide, p is 0 or 1, n is an integer, x is an oxygen atom, NH, methyleneoxy, methyleneamino or methylene-$(C_1-C_4)$-alkylamino and Y is an oxygen atom or NH, and the active compound is an anthracycline compound having biological action linked via a hydroxyl, amino or imino group;

(2) sugar or sugar alcohol; and (3) a pharmaceutically tolerable carrier.

2. A composition as claimed in claim 1, further comprising divalent ions.

3. A composition as claimed in claim 1, wherein the compound of the formula I or a physiologically tolerable salt thereof is employed in which W is a phenyl radical or a polysubstituted phenyl radical, and where the substituent, R is a hydrogen atom, methyl, methoxy, carboxyl, methyloxycarbonyl, CN, hydroxyl, nitro, fluorine, chlorine, bromine, sulfonyl, sulfonamide or sulfon-$(C_1-C_4)$-alkylamide and p is 0 or 1, n is 1 to 4, X is an oxygen atom, NH, methyleneoxy, methyleneamino or methylene-$(C_1-C_4)$-alkylamino, Y is an oxygen atom or NH, and the active compound is an anthracycline compound having biological action linked via a hydroxyl, amino or imino group.

4. A composition as claimed in claim 1, wherein the sugar or sugar alcohol comprises glucose, mannose, fructose, galactose, ribose, erythrose, glyceraldehyde, sedoheptulose, glucosamine, galactosamine, glucuronic acid, galacturonic acid, gluconic acid, galactonic acid, mannonic acid, glucitol, mannitol, sorbitol, glycerol or inositol.

5. A composition as claimed in claim 2, wherein the divalent ions are metal ions of Ca, Mg, Fe, Cu or Ni.

6. A composition as claimed in claim 1, wherein the composition comprises $Ca^{2+}$ ions, mannitol and compound II:

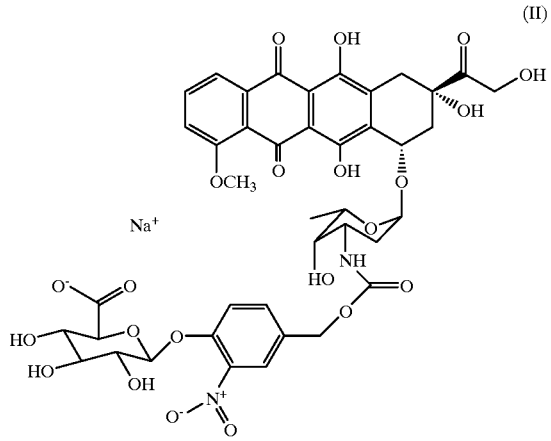

(II)

7. A composition as claimed in claim 6, wherein the composition is in solution and the amount of $CaCl_2 \times 2H_2O$ is about 0.4 mg/mL, the amount of mannitol is about 50 mg/mL, and the amount of compound II is about 25 mg/mL.

8. A composition as claimed in claim 1, comprising a compound of the formula I or a physiologically tolerable salt thereof, wherein
 glycosyl is a poly-, oligo- or monosaccharide, an alpha- or beta-O-glycosidically linked D-glucuronyl, D-glucopyranosyl, D-galacto pyranosyl, N-acetyl-D-glucosaminyl, N-acetyl-D-galactosaminyl, D-mannopyranosyl or L-fucopyranosyl radical,
 W is a phenyl radical or a monosubstituted phenyl radical, where the substituent,
 R is methoxy, methyloxycarbonyl, CN, hydroxyl, nitro, fluorine, chlorine, bromine, sulfonyl or sulfonamide and the others are a hydrogen atom,
 X is O, NH, methyleneoxy, methyleneamino or methylenemethylamino,
 Y is O or NH, and the active compound is an anthracycline compound having biological action linked via a hydroxyl, amino or imino group.

9. A process for the production of the composition as claimed in claim 1, which comprises processing the compound of the formula I or a physiologically tolerable salt thereof, sugar or sugar alcohol, optionally divalent ions, and a pharmaceutical carrier to give a pharmaceutical administration form.

10. A method of treatment of an autoimmune or inflammatory disorder of a human or an animal in need of such treatment, using a composition comprising:
 (1) a compound of the formula I or a physiologically tolerable salt thereof:

glycosyl-Y[—C(=Y)—X—]$_p$—W(R)$_n$—X—C(=Y)-active compound (I)

in which
 glycosyl is an enzymatically cleavable poly-, oligo- or monosaccharide,
 W is an aromatic or a heteroaromatic or an aliphatic having conjugated double bonds or an amino acid derivative which cyclizes after cleavage of the glycosyl radical, where the substituent
 R is a hydrogen atom, methyl, methoxy, carboxyl, CN, methylcarbonyl, hydroxyl, nitro, fluorine, chlorine, bromine, sulfonyl, sulfonamide or sulfon-($C_1$–$C_4$)-alkylamide,
 p is 0 or 1,
 n is an integer,
 X is an oxygen atom, NH, methyleneoxy, methyleneamino or methylene-($C_1$–$C_4$)-alkylamino and
 Y is an oxygen atom or NH, and the active compound is an anthracycline compound having biological action linked via a hydroxyl, amino or imino group;
 (2) sugar or sugar alcohol; and
 (3) a pharmaceutically tolerable carrier.

11. A method of treatment of a tumor in a human or an animal in need of such treatment, using a composition comprising:
 (1) a compound of the formula I or a physiologically tolerable salt thereof:

glycosyl-Y[—C(=Y)—X—]$_p$—W(R)$_n$—X—C(=Y)-active compound (I)

in which
 glycosyl is an enzymatically cleavable poly-, oligo- or monosaccharide,
 W is an aromatic or a heteroaromatic or an aliphatic having conjugated double bonds or an amino acid derivative which cyclizes after cleavage of the glycosyl radical, where the substituent
 R is a hydrogen atom, methyl, methoxy, carboxyl, CN, methylcarbonyl, hydroxyl, nitro, fluorine, chlorine, bromine, sulfonyl, sulfonamide or sulfon-($C_1$–$C_4$)-alkylamide,
 p is 0 or 1,
 n is an integer,
 X is an oxygen atom, NH, methyleneoxy, methyleneamino or methylene-($C_1$–$C_4$)-alkylamino and
 Y is an oxygen atom or NH, and the active compound is an anthracycline compound having biological action linked via a hydroxyl, amino or imino group;
 (2) sugar or sugar alcohol; and
 (3) a pharmaceutically tolerable carrier.

12. A method as claimed in claim 11, wherein the composition further comprises $Ca^{2+}$ ions, mannitol and compound II:

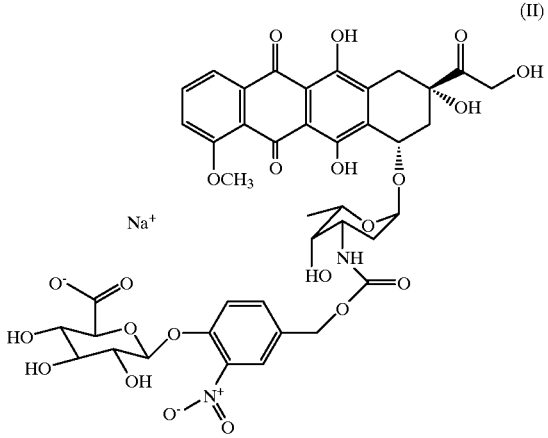

(II)

13. A method as claimed in claim 12 wherein the composition is in solution and the amount of $CaCl_2 \times 2H_2O$ is about 0.4 mg/mL, the amount of mannitol is about 50 mg/mL, and the amount of compound II is about 25 mg/mL.

14. A composition as claimed in claim 1, wherein said anthracycline is doxorubicin, 4'-epi-doxorubicin, 4-deoxydoxorubicin, or 4'-deoxydoxorubicin.

* * * * *